United States Patent [19]
Barnholtz

[11] Patent Number: 5,830,558
[45] Date of Patent: Nov. 3, 1998

[54] MULTIPLE PLY TISSUE PAPER HAVING PILES WITH AND WITHOUT CONTINUOUS NETWORK REGIONS

[75] Inventor: Steven Lee Barnholtz, Hamilton, Ohio

[73] Assignee: Procter & Gamble Company, Cincinnati, Ohio

[21] Appl. No.: 893,119

[22] Filed: Jul. 15, 1997

Related U.S. Application Data

[63] Continuation of Ser. No. 652,057, May 23, 1996, abandoned.

[51] Int. Cl.$^6$ ........................................................ B32B 5/14
[52] U.S. Cl. ............................ 428/171; 428/154; 428/195; 428/212; 428/219; 428/284; 428/297; 428/248; 428/178; 428/166; 428/535
[58] Field of Search ................................... 428/154, 195, 428/198, 212, 219, 284, 297, 298, 535, 156, 171, 178, 324, 553, 582, 166

[56] References Cited

U.S. PATENT DOCUMENTS

| | | |
|---|---|---|
| 3,414,459 | 12/1968 | Wells . |
| 3,547,723 | 12/1970 | Gresham . |
| 3,556,907 | 1/1971 | Nystrand . |
| 3,650,882 | 3/1972 | Thomas . |
| 3,708,366 | 1/1973 | Donnelly . |
| 3,738,905 | 6/1973 | Thomas . |
| 3,867,225 | 2/1975 | Nystrand . |
| 4,100,017 | 7/1978 | Flautt, Jr. ................................ 162/111 |
| 4,166,001 | 8/1979 | Dunning et al. . |
| 4,469,735 | 9/1984 | Trokhan . |
| 4,513,051 | 4/1985 | Lavash .................................... 428/212 |
| 4,610,915 | 9/1986 | Crenshaw et al. ...................... 428/219 |
| 5,468,325 | 11/1995 | McNeil .................................... 156/209 |

*Primary Examiner*—Merrick Dixon
*Attorney, Agent, or Firm*—Jay A. Krebs; Larry L. Huston; E. Kelly Linman

[57] ABSTRACT

A multiple ply tissue paper structure is disclosed. The paper structure includes a ply comprising discrete relatively low density regions dispersed throughout a relatively high density continuous network. The paper structure also include a ply which does not include discrete relatively low density regions dispersed throughout a relatively high density continuous network. The different structures of the two plies provide improved absorbency over a homogeneous multiple ply structure.

10 Claims, 6 Drawing Sheets

MULTIPLE PLY TISSUE PAPER HAVING PILES WITH AND WITHOUT CONTINUOUS NETWORK REGIONS

This is a continuation of application Ser. No. 08/652,057, filed on May 23, 1996, now abandoned.

FIELD OF THE INVENTION

The present invention is related to a tissue paper structure, and more particularly, to multiple ply tissue paper structures.

BACKGROUND OF THE INVENTION

Paper webs made from cellulosic fibers are used in consumer products such as paper towels, toilet tissue, and facial tissue. Multiple ply paper structures are well known in the art. Such multiple ply structures have two or more plies which are positioned in face to face relationship and joined together. Each ply can be formed from a paper web. A paper web can have one or more layers as it is formed on a paper machine, as is also well known in the art.

The individual plies of a multiple ply paper structure can be joined in any number of suitable ways, including adhesive bonding or mechanical bonding, such as by embossing. Frequently, plies are embossed for aesthetic reasons, to provide space between adjacent plies, and to connect adjacent plies in face to face relationship.

Examples of multiple ply paper structures are shown in the following references: U.S. Pat. No. 3,650,882 issued March, 1972 to Thomas; U.S. Pat. No. 4,469,735 issued September, 1984 to Trokhan; and U.S. Pat. No. 3,953,638 issued April 1976 to Kemp. The following references disclose embossing or embossed products or multiple ply paper products: U.S. Pat. No. 5,490,902 issued Feb. 13, 1996 to Shulz; U.S. Pat. Nos. 5,468,323 issue November 1995 to McNeil and commonly assigned; 4,300,981 issued November 1981 to Carstens; 3,414,459 issued Dec. 3, 1968 to Wells and commonly assigned; 3,547,723 issued Dec. 15, 1970 to Gresham; 3,556,907 issued Jan. 19, 1971 to Nystrand; 3,708,366 issued Jan. 2, 1973 to Donnelly; 3,738,905 issued Jun. 12, 1973 to Thomas; 3,867,225 issued Feb. 18, 1975 to Nystrand and 4,483,728 issued Nov. 20, 1984 to Bauernfeind. Commonly assigned U.S. Pat. No. Des. 239,137 issued Mar. 9, 1976 to Appleman illustrates an emboss pattern found on commercially successful paper toweling.

It is generally understood that a multiple ply structure can have an absorbent capacity greater than the sum of the absorbent capacities of the individual single plies which make up the multiple ply structure. Above referenced U.S. Pat. No. 3,650,882 to Thomas discloses a three ply product which is said to have a water absorbtion capacity which is more than double that of two ply towels of similar furnish, and which is said to have an absorbent capacity which is greater than would be expected from a simple consideration of the additional amount of material in a three ply structure.

However, comparison of the absorbent capacity of a multiple ply structure to the absorbent capacities of single ply paper structures, or other multiple ply paper structures having fewer plies, is not especially helpful in judging the performance of the multiple ply product. The absorbent capacity gained by adding an additional ply is generally greater than absorbent capacity held within the added ply. This difference is due, at least in part, to the inter-ply storage space created by the addition of an extra ply.

A heterogeneous n ply product having plies obtained from different types of substrates is normally expected to have an absorbent capacity which is no greater than the arithmatic mean of the absorbent capacities measured for the homogeneous n ply structures formed from the different substrates. For instance, a heterogeneous two ply tissue product has a first ply formed from a first type of paper substrate and a second ply formed from a second, different type of paper substrate. The absorbent capacity of such a heterogeneous two ply product is generally expected to be less than or equal to the arithmatic mean of the absorbent capacities measured for 1) a homogeneous two ply structure formed from two plies of the first substrate and 2) a homogeneous two ply structure formed from two plies of the second substrate.

Above referenced U.S. Pat. No. 4,469,735 discloses extensible multiply tissue paper products. The products of U.S. Pat. No. 4,469,735 are said to have synergistically high liquid absorbency by virtue of at least two plies of the product having sufficiently different stress/strain properties. However, it is desirable to be able to provide improved absorbency without the need to impart different stress/strain properties to different plies.

Accordingly, one object of the present invention is to provide a multiple ply paper structure having improved absorbent properties.

Another object of the present invention is to provide a multiple ply paper structure which achieves a higher absorbent capacity and rate than anticipated with respect to other paper structures having the same number of plies.

Another object of the present invention is to provide a multiple ply paper structure having plies with different texture values and calipers.

Another object of the present invention is to provide a multiple ply paper structure having one or more plies having discrete, low density regions dispersed in a continuous network region.

SUMMARY OF THE INVENTION

The present invention provides a heterogeneous multiple ply tissue paper product having n plies, where n is an integer greater than or equal to 2. The heterogeneous multiple ply tissue paper product includes a first ply comprising a paper web having a continuous network region having a relatively high density and discrete relatively low density regions dispersed throughout the continuous network region. The paper product also has a second ply, wherein the second ply does not include relatively low density regions dispersed throughout a continuous network region.

The first ply can have a caliper which is at least about 1.25 times, more particularly at least about 1.5 times, even more particularly at least about 2.0 times the caliper of the second ply.

The different structures of the plies can provide the heterogeneous multiple ply tissue paper product with a horizontal absorbent capacity which is greater than the mean of the homogeneous n ply absorbent capacities of the n plies, without the need for imparting different stress/strain properties to the plies, as described in above referenced U.S. Pat. No. 4,469,735.

The heterogeneous multiple ply tissue paper product can include at least one ply having a macro-density which is at least about 1.5 times, more preferably at least about 2.0 times, more preferably at least about 2.5 times, and even more preferably at least about 3.0 times the macro-density of at least one of the other n plies.

DETAILED DESCRIPTION OF THE INVENTION

Figure 1A:
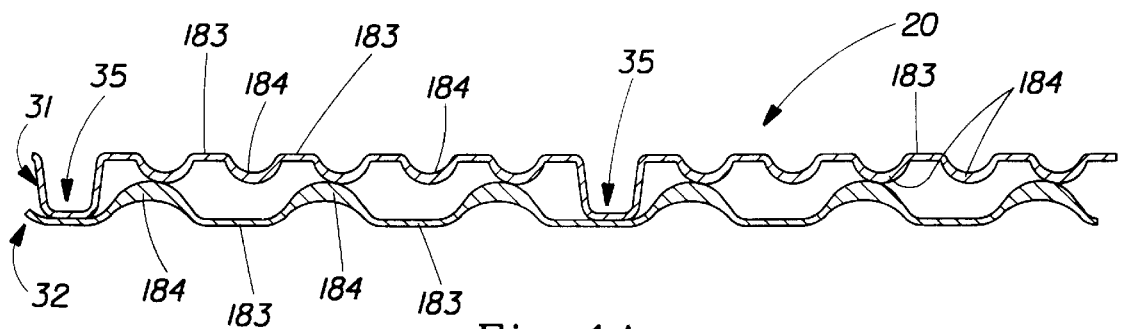
FIG. 1A is a cross-sectional illustration of a 2 ply paper structure having relatively large domes facing inwardly.
Figure 1B:
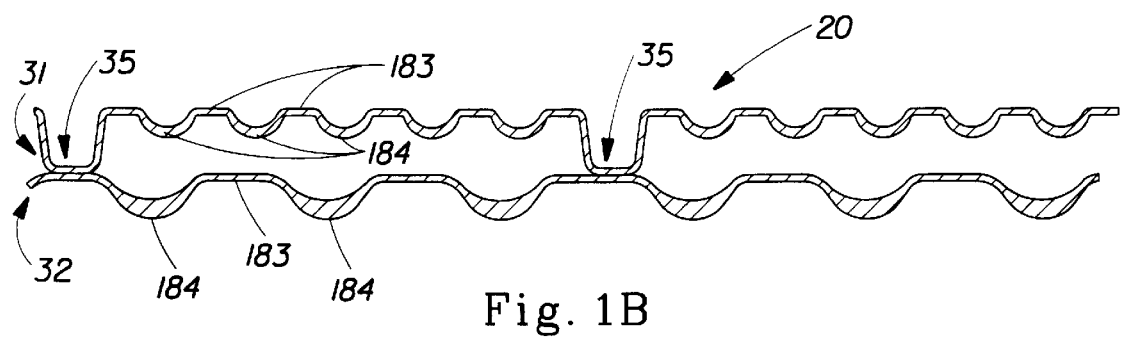
FIG. 1B is a cross-sectional illustration of a 2 ply structure having relatively large domes facing outwardly.
Figure 2A:
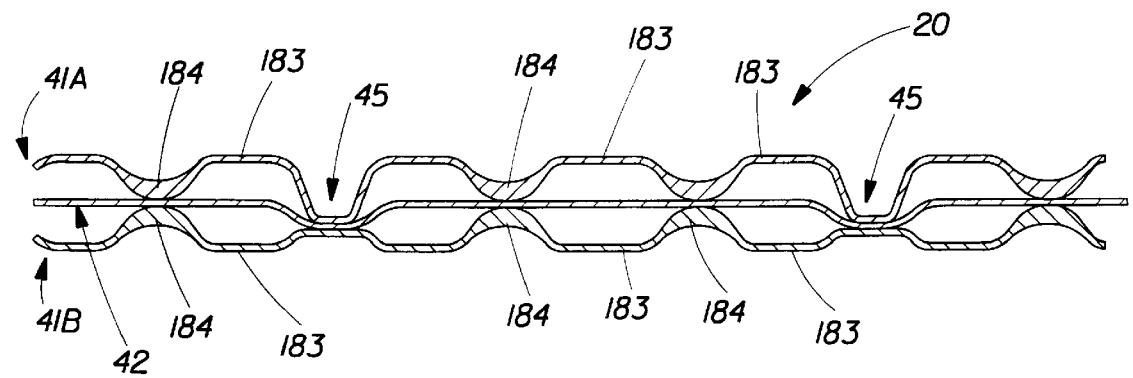
FIG. 2A is a cross-sectional illustration of a 3 ply structure having a relatively low texture, non-patterned ply disposed between relatively highly textured, patterned plies.
Figure 2B:
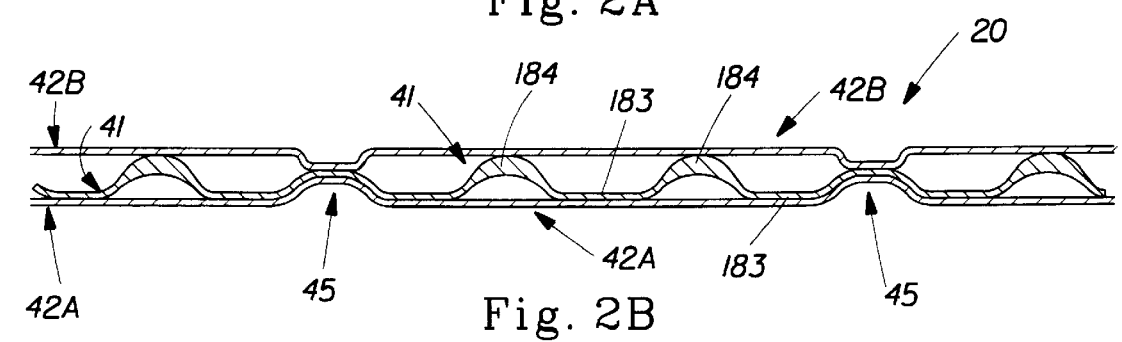
FIG. 2B is a cross-sectional illustration of an alternative 3 ply embodiment having a relatively highly textured, patterned ply disposed between relatively low texture, non-patterned plies.

The present invention comprises a heterogeneous multiple ply tissue paper product 20 having n plies. FIGS. 1A and 1B are cross-sectional illustrations of 2 ply structures (n=2). The individual plies in FIG. 1A are designated 31 and 32, respectively. The plies 31 and 32 are joined at discrete, spaced apart locations by embossments 35. FIGS. 2A and 2B are cross-sectional illustration of 3 ply embodiments (n=3) of the present invention. The individual plies in FIG. 2A are designated 41A, 42, and 41B. The plies 41A, 42, and 41B are joined together at discrete, spaced apart locations by embossments 45.

By the term "heterogeneous multiple ply tissue paper product" it is meant that at least one of the plies of the multiple ply tissue product 20 can be distinguished from at least one of the other n plies in terms of at least one of the following properties: caliper, macro-density, basis weight, or texture value. The caliper, macro-density, basis weight, and texture value of a ply are measured according to the procedures provided below.

A homogeneous multiple ply paper structure is a multiple ply structure having plies which are made with substantially the same composition of paper fiber furnish and papermaking additives, and which are all substantially identical to one another with respect to all of the above properties (i.e. for any of the above properties, the maximum ply to ply difference of that particular property is less than about 10 percent of the lower value of the property).

The absorbent capacity and absorbent rate of the heterogeneous multiple ply tissue paper product 20 are measured according to the procedures described below. The heterogeneous multiple ply tissue paper products 20 of the present invention can have an absorbent capacity which is greater than the weighted average of the homogeneous n ply absorbent capacities measured for each of the n plies. In one embodiment, the heterogeneous multiple ply tissue paper products of the present invention can have an absorbent capacity which is greater than the maximum of the homogeneous n ply absorbent capacities measured for the n plies. The heterogeneous multiple ply tissue paper products of the present invention can have a wicking capacity which is greater than the weighted average of the homogeneous n ply wicking capacities measured for each of the n plies. The heterogeneous multiple ply tissue paper products of the present invention can also have an absorbent rate which is greater than the weighted average of the homogeneous n ply absorbent rates measured for each of the n plies.

The "homogeneous n ply absorbent capacity" and the "homogeneous n ply absorbent rate" for a particular ply are determined as follows. First, a "homogeneous n ply structure" for that particular ply is formed by joining together n plies of that particular ply. This multiple ply structure is referred to as a "homogeneous n ply structure" because all the plies are substantially identical. N plies of the particular ply are joined together using the same procedure (eg same embossing method, same embossing pattern, same adhesive) used to combine the n plies of the heterogeneous multiple ply tissue paper product. A homogeneous n ply structure is formed for each different ply used to form the heterogeneous multiple ply tissue paper product.

Then, the absorbent capacity and the absorbent rate for each of the homogeneous n ply structures are measured. The absorbent capacity and absorbent rate of each homogeneous n ply structure is measured using the same procedures used to measure the absorbent capacity and absorbent rate for the heterogeneous multiple ply tissue paper product. Accordingly, the absorbent capacity and absorbent rate of the heterogeneous multiple ply tissue paper product can be compared to those of homogeneous multiple ply structures having the same number of plies. Averages can then be calculated for the homogenous n ply absorbent capacities and rates.

For example, referring to FIG. 1A, the heterogeneous multiple ply tissue paper product 20 has two plies, 31 and 32 (n=2), where ply 32 is not obtained from the same type of paper web from which ply 31 is obtained. For instance, ply 32 can have a caliper, macro-density, and texture value substantially different from those of ply 31. The associated homogeneous 2 ply structure for ply 31 is obtained by joining together two paper webs of the type from which the ply 31 is formed. Likewise, the associated homogeneous 2 ply structure for ply 32 is obtained by joining together two paper webs of the type from which the ply 32 is formed. The homogenous 2 ply paper structures are formed using the same combining method (eg. same adhesive, same embossing method, same embossing pressure, same embossing pattern, etc.) which is used to combine the plies 31 and 32 together to form the heterogeneous 2 ply paper product 20.

The absorbent capacity and absorbent rate can then be measured for the homogeneous 2 ply structure for ply 31.

Likewise, the absorbent capacity and rate can be measured for the homogeneous 2 ply structure for ply 32. For the structure of FIG. 1A, the average of the homogeneous n ply absorbent capacities is the average of the absorbent capacities measured for the homogeneous 2 ply structure for ply 31 and the homogenous 2 ply structure for ply 32. Similarly, the average of the homogeneous n ply absorbent rates is the mean of the absorbent rates measured for the homogeneous 2 ply structure for ply 31 and the homogeneous 2 ply structure for ply 32.

Referring to FIG. 2A, the heterogeneous multiple ply tissue paper product 20 has three plies, 41A, 42, and 41B (n=3). Ply 41A is obtained from a paper web of the same type from which ply 41B is obtained, and ply 42 is obtained from a paper web different from that of the type from which plies 41A and 41B are obtained. The associated homogeneous 3 ply structure for plies 41A and 41B is obtained by joining together three paper webs of the type from which the ply 41A is formed. Likewise, the associated homogeneous 3 ply structure for ply 42 is obtained by joining together three paper webs of the type from which the ply 42 is formed. The homogenous 3 ply paper structures are formed using the same combining method (eg. same adhesive, same embossing method, same embossing pressure, same embossing pattern, etc.) which is used to combine the plies 41A, 42, and 41B together to form the heterogeneous 3 ply paper product 20.

The absorbent capacity and absorbent rate can then be measured for the homogeneous 3 ply structure for ply 41A. Likewise, the absorbent capacity and absorbent rate can be measured for the homogeneous 3 ply structure for ply 42. For the structure of FIG. 2A having ply 41A made from a paper web of the same type from which ply 41B is formed, the average of the homogenous n ply absorbent capacities can be calculated as a weighted average of the homogeneous n ply absorbent capacities:

$$[(2)\times(AC41A)+(AC42)]/3$$

where AC41A is the homogeneous 3 ply absorbent capacity for ply 41A (or for ply 41B), and AC42 is the homogeneous 3 ply absorbent capacity for ply 42.

Likewise, the average of the homogeneous n ply absorbent rates can be calculated as a weighted average of the homogeneous n ply absorbent rates:

$$[(2)\times(AR41A)+(AR42)]/3$$

where AR41A is the homogeneous 3 ply absorbent capacity for ply 41a (or for ply 41B) and AR42 is the homogeneous 3 ply absorbent capacity for ply 42.

Without being limited by theory, it is believed that the multiple ply products of the present invention can provide the improved absorbency and absorbency rate due, at least in part, to their combination of a relatively highly textured, high caliper, relatively low macro-density ply with a relatively lower textured, low caliper, relatively higher macro-density ply. Such different characteristics can be imparted to paper webs, at least in part, through the selective use of papermaking fabrics and methods. In particular, the texture value is a measure of the wet formed, non-mechanically embossed texture of the surface of a ply prior to combining the ply with other plies.

The texture value does not include mechanically embossed features. Such embossed features imparted to the web when after it is dried may be at least partially destroyed when the web is wetted. Wet formed texture features imparted to the ply while the ply is on the paper machine (such as those imparted to a web by through air drying on the drying fabric of a papermachine or by wet pressing prior to drying) are included in the texture measurement. Such wet formed texture features can better maintain their structure when wetted, especially when a wet strength additive, such as KYMENE, is added to the furnish from which the web is formed.

Figure 3:
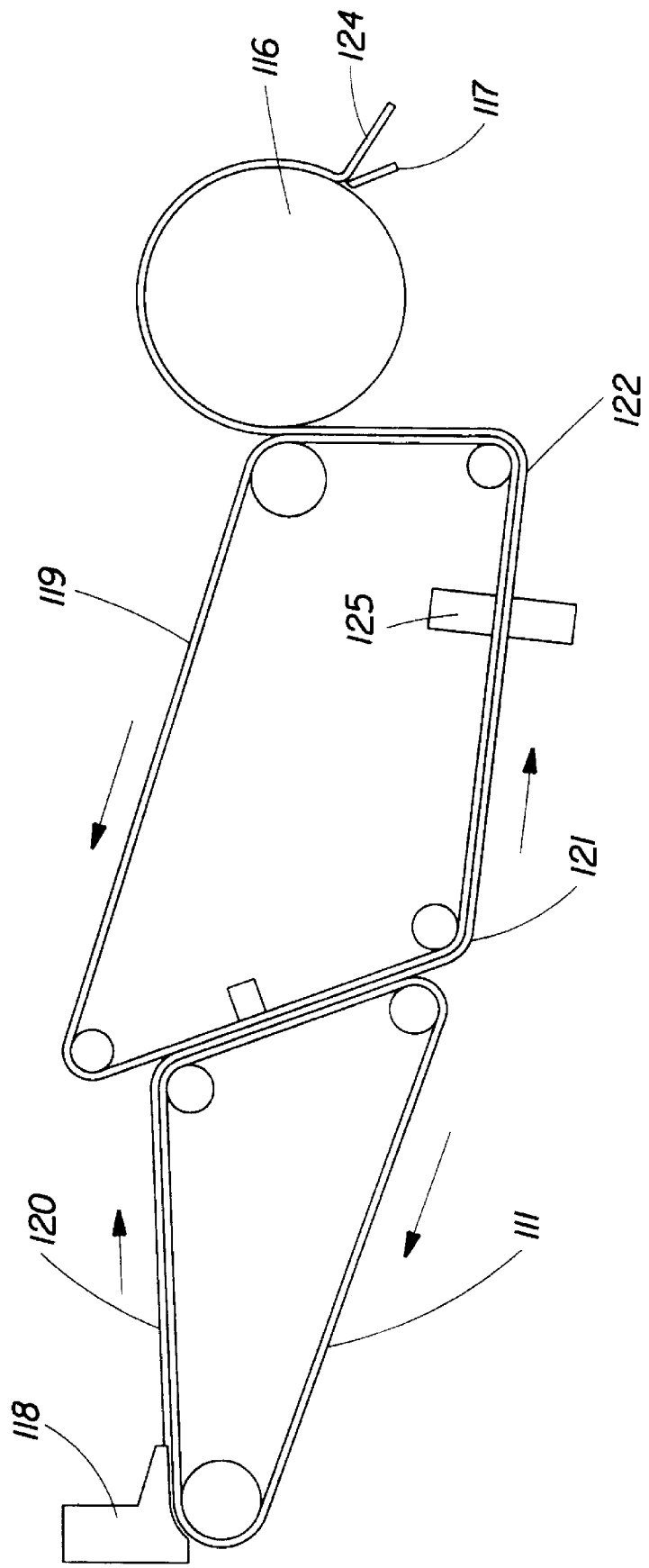
FIG. 3 is a schematic illustration of a paper making machine.

FIG. 3 is an illustration of a paper machine for use in making a paper web. The paper webs made on such a paper machine can be used to form the individual plies of a multiple ply product. Referring to FIG. 3, a headbox 118 delivers the aqueous dispersion of papermaking fibers to a foraminous member 111. The foraminous member 111 can be in the form of an endless belt which is carried in the direction indicated about a series of rolls. The foraminous member 111 can comprise a fourdrinier wire.

Alternatively, the foraminous member 111 can comprise a plurality of discrete protuberances joined to a reinforcing structure, each protuberance having an orifice. Such a forming member 111 is suitable for providing a web having different basis weight regions, and is described generally in U.S. Pat. No. 5,503,715 issued Apr. 2, 1996 to Trokhan et al., which patent is incorporated by reference.

After the dispersion of fibers is deposited on the forming member 111, an embryonic web 120 is formed by removal of a portion of the water from the dispersion. Removal of the water can be accomplished by techniques well known in the art, such as by vacuum boxes, forming boards, and the like.

The embryonic web 120 is then transferred to a drying member 119, which is in the form of an endless belt carried about a series of rolls in the direction shown. The n ply structures of the present invention can have plies having about the same level of wet-foreshortening (within about 5 percent). For the purpose of making a paper structure according to the present invention, the web can be wet-foreshortened less than about 5 percent, with wet-foreshortening of the web on transfer to the drying member 119 being about 3 percent. Wet-foreshortening is described in U.S. Pat. No. 4,469,735, which patent is incorporated herein by reference.

The embryonic web can be dewatered as it is transferred to the drying member 119. The resulting intermediate web 121 is carried on the drying member 119 in the direction shown in FIG. 3. The web can then be further dried as it is carried on the drying member 119. For instance, when the drying member is in the form of a foraminous belt (such as is described in U.S. Pat. No. 4,529,480 to Trokhan and U.S. Pat. No. 4,191,609 to Trokhan), the web can be dried using through air drying equipment 125 to provide a predried web 122. Alternatively, if the drying member 119 is a conventional papermaker's dewatering felt, the web can be further dewatered by pressing the web in nip as the web is carried on the felt. In yet another embodiment, the web can be dewatered by wet pressing the web as described in WO 95/17548 "Wet Pressed Paper Web and Method of Making Same" published Jun. 29, 1995 in the name of Ampulski et al., which publication is incorporated herein by reference.

The predried web can then be transferred to the surface of a heated drying drum 116 for further drying. The web can then be creped from the surface of the drum 116, such as by use of a doctor blade 117, to provide a dried paper web 124. Use of the doctor blade 117 provides a web 124 which is dry-foreshortened (i.e. dry creped). For the purpose of making a paper structure according to the present invention, the web can be dry-foreshortened less than about 16 percent, with dry foreshortening of the web being about 10 percent in one embodiment. Accordingly, paper made according to the present invention can have relatively low levels of wet foreshortening and dry foreshortening.

The multiple ply tissue paper product of the present invention can include at least one ply comprising a paper web having regions of different density. In one embodiment, the multiple ply tissue product of the present invention can comprise a ply formed from a paper web having discrete regions of relatively high density dispersed throughout one or more regions of relatively low density. For instance, such a web can be formed on a papermachine such as that shown in FIG. 3. The discrete regions of relatively high density can be formed by transferring the embryonic web to a dryer member 119 in the form of a woven fabric having discrete compaction knuckles. The compaction knuckles can be disposed at the cross over points of warp and shute filaments of the fabric. The compaction knuckles serve to densify discrete, spaced apart portions of the web as the web is transferred to the drying drum 116. The following patents are incorporated by reference for the purpose of showing drying fabrics and/or methods for forming a paper web having regions of different density, and more particularly, a textured paper web having discrete, relatively high density regions disposed throughout one or more relatively low density regions. U.S. Pat. No. 3,301,746 issued January, 1967 to Sanford et al.; U.S. Pat. No. 3,974,025 issued August, 1976 to Ayers; U.S. Pat. No. 3,994,771 issued November 1976 to Morgan et al; and U.S. Pat. No. 4,191, 609 issued March 1980 to Trokhan. U.S. Pat. No. 4,191,609 is particurarly preferred for forming a paper web having an array of uncompressed, relatively low density regions which are in staggered relation in both the machine and cross machine directions.

In one embodiment, at least one of the plies of the heterogeneous multiple ply tissue paper structure comprises a paper web made according to the teachings of EP 0677612A2 published Oct. 18, 1995 in the name of Wendt et al., which application is incorporated herein by reference.

Figure 4:
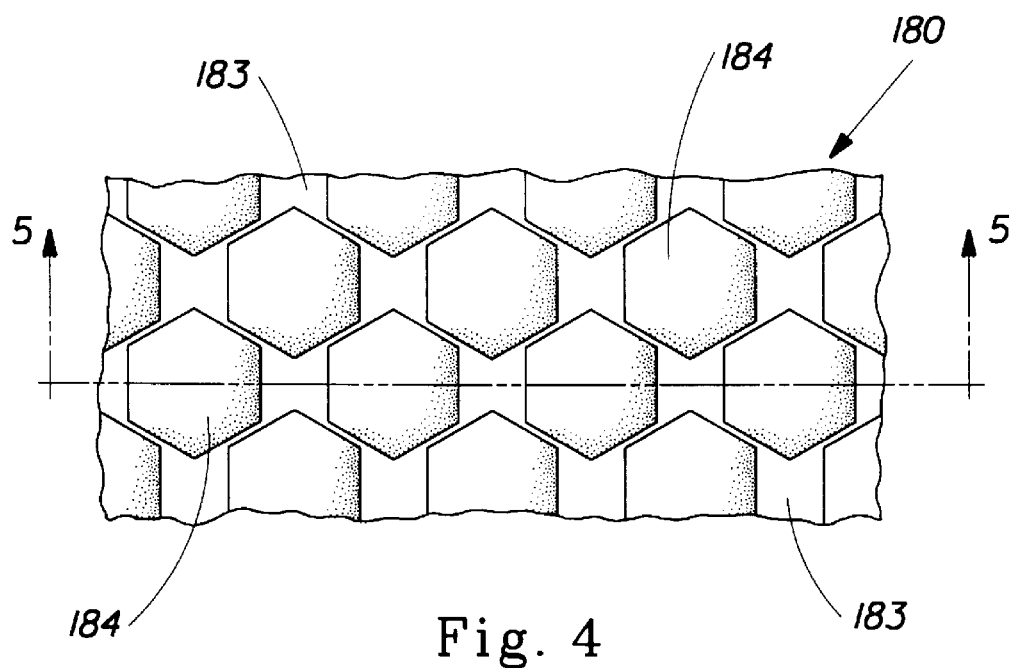
FIG. 4 is a plan view of a paper web having a continuous network region and discrete domes.
Figure 5:
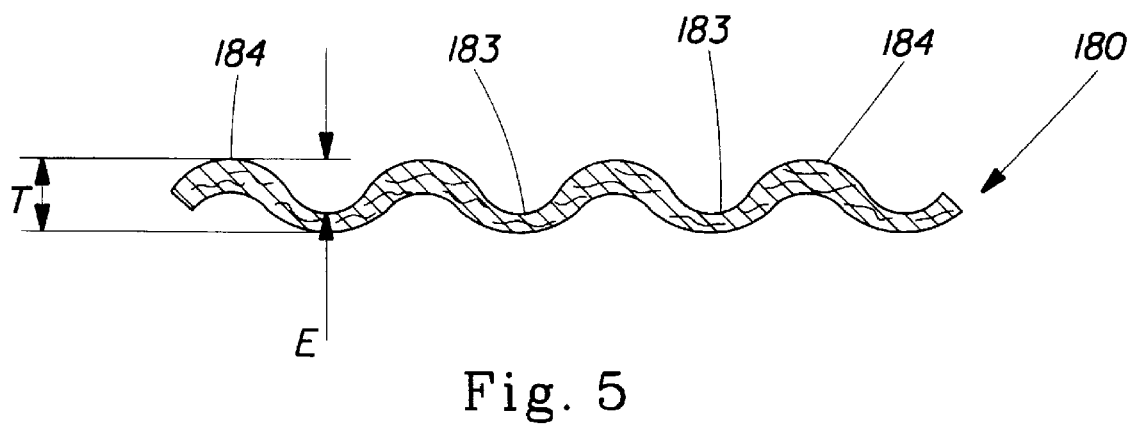
FIG. 5 is a cross-sectional view of the paper web of FIG. 4 taken along lines 5—5 in FIG. 4.

In one embodiment, at least one of the plies of the heterogeneous multiple ply tissue paper structure comprises a paper web having a continuous network region having a relatively low basis weight and a relatively high density; and a plurality of discrete regions dispersed throughout the continuous network region, the discrete regions having relatively high basis weights and relatively low densities. A ply comprising a paper web 180 having a continuous network region 183 having a relatively low basis weight and a relatively high density, and discrete domes 184 having relatively high basis weights and relatively low densities is shown in FIGS. 4 and 5. The caliper of the ply is designated as T in FIG. 5.

Such a paper web is shown and described in U.S. Pat. No. 4,529,480 issued Jul. 16, 1985 to Trokhan. Trokhan '480 also discloses a drying member 119 in the form of a foraminous belt suitable for making such a web. The drying member 119 shown in Trokhan '480 has a macroscopically monoplanar, patterned, continuous network surface defining a plurality of discrete, isolated, non-connecting deflection conduits. The following U.S. Patents are incorporated herein by reference for the purpose of describing such a foraminous belt: U.S. Pat. No. 4,514,345 to Johnson et al.; U.S. Pat. No. 4,529,480 to Trokhan; U.S. Pat. No. 5,364,504 to Smurkoski et al.; U.S. Pat. No. 5,514,523 to Trokhan et al.

Referring back to FIG. 1A, a heterogeneous 2 ply tissue paper product can have plies 31 and 32, wherein at least one of the plies has a continuous network region 183 and a plurality of discrete domes 184. FIG. 1A shows both plies comprising paper webs having a continuous network region 183 and a plurality of discrete domes 184. Both of the plies 31 and 32 are patterned, having domes 184 which extend inwardly (i.e. the domes 184 of ply 31 face the domes 184 of ply 32.). The domes 184 of ply 31 can have the same shape as the domes of ply 32, or the domes 184 of ply 31 can have a shape which is different from that of the domes of ply 32. The domes in each of the plies can be bilaterally staggered.

In FIG. 1A, ply 31 is different from ply 32 in that ply 31 has a relatively larger number of relatively smaller domes 184 per unit area, while ply 32 has a relatively smaller number of relatively larger domes 184 per unit area. In particular, ply 31 can have X domes 184 per square inch, where the value of X is at least about 100. Ply 32 can have Y discrete domes 184 per square inch, where the value of Y is less than the value of X, and the value of Y is less than about 250. The ratio of X to Y can be at least about 1.5, at least about 2.0, and in one embodiment is at least about 10. In one embodiment, ply 31 can have at least about 200, and more particularly at least about 500 domes 184 per inch, and ply 32 can have less than about 110, and more particularly less than about 75 domes per square inch. In addition, ply 32 has a caliper which is greater than the caliper of ply 31. Ply 32 can have a caliper which is at least about 1.25 times, more particularly, at least about 1.5 times, even more particularly at least about 2.0 times, and in one embodiment at least about 2.5 times the caliper of ply 31.

Each of the plies 31 and 32 can have a basis weight of between about 7–60 lb/3000 square feet. In one embodiment, the plies 31 and 32 can each have a basis weight of about 12–15 pounds per 3000 square feet. The macro-density of ply 31 can be at least about 1.5 times, more preferably at least about 2.0 times, and even more preferably at least about 2.5 times the macro-density of ply 32.

Ply 32 has a texture value greater than ply 31. In one embodiment, the ply 32 can have a texture value which is at least about 1.5 times, more preferably at least about 2.0 times, and even more preferably at least about 4.0 times the texture value of ply 31. In particular, ply 32 can have a texture value of at least 15 mils, and ply 31 can have a texture value of less than about 10 mils. In one embodiment, the ply 32 can have a texture value of between about 23 and about 25 mils and ply 31 can have a texture value of between about 4.0 and about 6.0 mils. The texture value provides a measure of the wet formed surface characteristics provided by the drying member 119. In particular, the texture value can provide a measure of the difference in elevation between the domes 184 and the network 183.

In an alternative 2 ply embodiment shown in FIG. 1B, ply 32 can be joined to ply 31 such that the domes 184 of ply 32 face outwardly and the domes 184 of ply 31 face inwardly toward ply 32. In such a 2 ply structure, ply 31 can provide a relatively smooth outwardly facing surface, and ply 32 can provide a relatively highly textured outwardly facing surface having outwardly facing protrusions in the form of the domes 184. The relatively highly textured outwardly facing surface of ply 32 can be useful in scrubbing or scouring operations, while the relatively smooth outwardly facing surface of ply 31 can be used for wiping liquid from a surface.

Alternatively, the two ply structure 20 can comprise one ply having a continuous network and discrete domes, and a second ply which does not include discrete domes dispersed throughout a continuous network. For instance, the ply 31 in FIG. 1A or 1B can be replaced by a ply of the type shown as ply 42 in FIG. 2A.

Referring to FIG. 2A, one embodiment of the present invention is a heterogeneous 3 ply tissue paper product having plies 41A, 42, and 41B. The plies 41A and 41B can have substantially the same structure and composition. Each of the plies 41A and 41B can be patterned to have a continuous network region 183 and a plurality of discrete domes 184. Each of the plies 41A and 41B can have the same number Y of domes 184 per square inch. The value of Y can be between about 10 and about 600, and more particularly between about 10 and about 200. Ply 42 can be formed from a web of conventional felt dried tissue paper having substantially unpatterned smooth, untextured surfaces, and a generally uniform density and basis weight (no discernable regions having different micro-densities or different micro-basis weights). Each of the surfaces of ply 42 can have a texture value of less than about 1.0.

In the embodiment shown in FIG. 2A, each of the plies 41A and 41B has a caliper greater than that of ply 42, and each of the plies 41A and 42B has a macro-density less than that of ply 42. The plies 41A and 41B can each have a caliper which is at least about 2.5 times that of ply 42. The ply 42 can have a macro-density which is at least about 2.5 times that of plies 41A and 41B. Ply 42 can have a texture value less than about 1.0, and plies 41A and 41B can each have a texture value of at least about 10.

In one embodiment, each ply 41A and 41B can have a basis weight of about 13.6 pound/3000 square feet, a caliper of at least about 20 mils, and a macro density of less than about 1.0 pounds/ mil-3000 square feet. Ply 41A and 41B can each have a texture value of at least about 15 mils, and can have about 75 domes 184 per square inch. Ply 42 can have a basis weight of about 12.5 pound/3000 square feet, a caliper of between about 4 and about 6 mils, a macro density of at least about 2.0 pounds/mil-3000 square feet, and a texture value of about zero.

In the alternative 3 ply embodiment of FIG. 2B, a patterned, relatively highly textured ply 41 can be disposed between two plies 42A and 42B having relatively low texture, the plies 42A and 42B having substantially no discernable pattern. In yet another 3 ply embodiment, a relatively higher textured ply, such as ply 41, can be disposed between two plies such as that shown as ply 31 in FIG. 1A. Each of the 3 plies in such a structure has relatively low density domes disposed throughout a continuous high density network.

Figure 6:
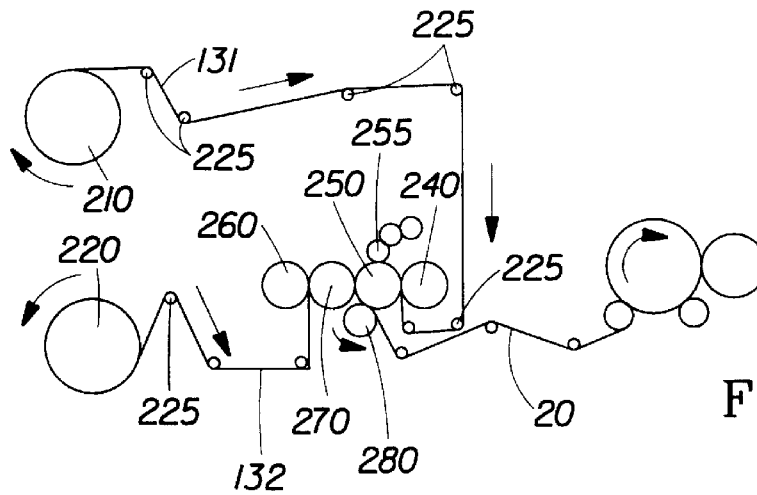
FIG. 6 is a schematic illustration of equipment for combining two separate plies to form a two ply product according to the present invention.

Two or more of the paper webs 131 and 132 having desired characteristics relative to one another are combined to provide the multiple ply tissue paper product of the present invention. FIG. 6 illustrates equipment that can be used to combine two webs having desired characteristics relative to one another in order to form a two ply product according to the present invention. Two single ply webs 131 and 132 are unwound from rolls 210 and 220, respectively. Each of the webs 131 and 132 can have regions of different density, and each ply can have a continuous network region having a relatively high density, and discrete domes having relatively low densities. The two webs 131 and 132 are carried in the directions indicated around rollers 225. Web 131 corresponds to ply 31 in FIG. 1, and web 132 corresponds to ply 32 in FIG. 1.

Web 131 is directed through a nip formed between a rubber roll 240 and a steel embossing roll 250, as web 132 is directed through a nip formed between rubber roll 260 and a steel embossing roll 270. In the embodiment of FIG. 1A, the domes 184 of the web 131 face roll 240, and the domes 184 of web 132 face roll 260, so that the domes 184 face inwardly in the resulting 2 ply structure. The steel embossing rolls 250 and 270 have a pattern of embossing pins which contact and deform selective, discrete portions of the webs 131 and 132, respectively. The web 131 is then carried through a nip formed between a glue applicator roll 255 and the steel embossing roll 250. The glue applicator roll, which has a surface which is continuously replentished with glue, transfers glue to the deformed portions of the web 131. Webs 131 and 132 then pass between steel embossing rolls 250 and 270, with web 131 adjacent roll 250 and web 132 adjacent roll 270. The embossing pins on roll 250 nest with those on roll 270 to deform the webs 131 and 132, and to provide nesting of web 131 with web 132.

The two webs 131 and 132 then pass through a nip having a pre-determined nip loading, the nip being formed between steel embossing roll 250 and a marrying roll 280. Marrying roll 280 has a hard rubber cover, and serves to press the webs 131 and 132 together to ensure bonding of web 131 to web 132 at those locations where adhesive is transferred from roll 255 to ply 131. The resulting two ply paper structure 20 can be rewound for later converting into smaller rolls.

Figure 7:
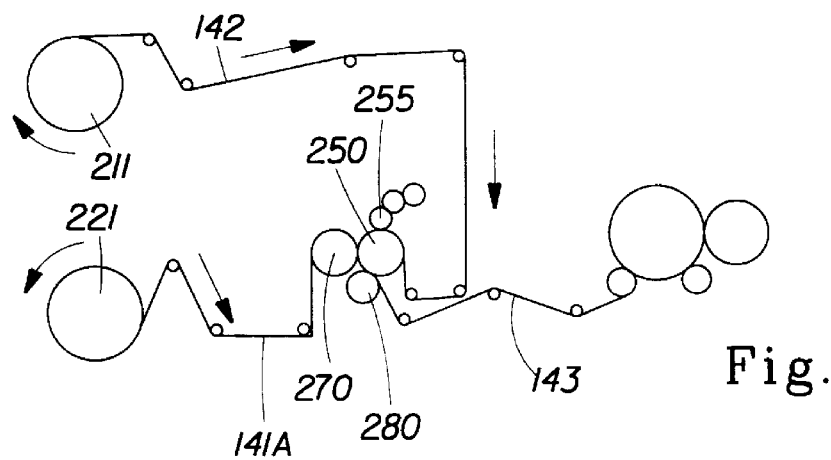
FIG. 7 is a schematic illustration of equipment for combining two plies to provide an intermediate 2 ply structure.
Figure 8:
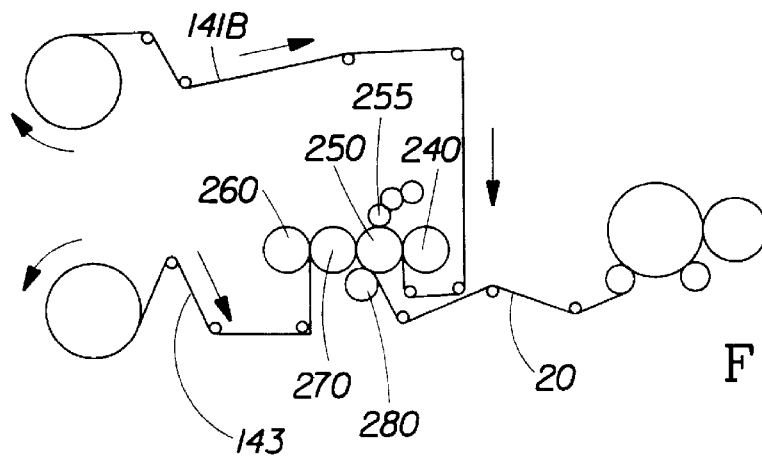
FIG. 8 is a schematic illustration of equipment for combining the intermediate 2 ply structure made according to FIG. 7 with a third ply to provide a 3 ply product according to the present invention.

FIGS. 7 and 8 illustrate combining three separate webs to provide a three ply paper structure such as that shown in FIG. 2A. Web 141A corresponds to ply 41A in FIG. 2A, web 142 corresponds to ply 42 in FIG. 2A, and web 141B corresponds to ply 41B in FIG. 2A. Webs 141A and 141B can have a continuous network region having a relatively high density and discrete domes having relatively low densities. Web 142 can comprise a conventional felt pressed web.

Webs 142 and 141A can be unwound from rolls 211 and 221, respectively, and carried in the directions shown. Web 142 is directed through a nip formed between glue applicator roll 255 and steel embossing roll 250 (The rubber embossing rolls 240 and 260 are disengaged in this operation) to transfer a layer of adhesive from roll 255 to web 142. Webs 131 and 132 then pass between steel embossing rolls 250 and 270, with web 142 adjacent roll 250 and web 141A adjacent roll 270. The embossing pins on roll 250 nest with those on roll 270. The two webs then pass through the nip formed between steel embossing roll 250 and marrying roll 280 to ensure bonding of web 141A to web 142, thereby providing an intermediate 2 ply structure designated 143 in FIGS. 7 and 8.

The web 141B can then be joined to the intermediate 2 ply structure 143, as shown in FIG. 8. Intermediate structure 143 is directed through the nip between rubber roll 260 and steel embossing roll 270 such that its constituent web 141A is positioned against roll 270 and its constituent web 142 is positioned against roll 260. Accordingly, web 142 is adhesively joined to web 141B when the three webs pass through the nip between marrying roll 280 and embossing roll 250.

EXAMPLES

Example 1

2 ply

The purpose of this example is to illustrate one method that can be used to form a two ply embodiment of the present invention. Each of the plies 31 and 32 are formed on a pilot scale paper machine having the general configuration shown in FIG. 3. A 0.1 percent consistency aqueous slurry of papermaking fibers, water, and additives is formed for deposition on the foraminous member 111. The aqeuous slurry comprises a mixture of 75:25 by weight NSK (northern softwook Kraft) and CTMP (chemi-thermo mechanical pulp) paper fibers. The additives include a wet strength additive, a dry strength additive, a wettability agent, and a softness additive. The wet strength additive comprises an effective amount of epichlorohydrin adduct in the form of about 22 pounds KYMENE 557H per ton of dry fiber weight. KYMENE 557H is supplied by Hercules Corp of Wilmington, Del. The dry strength additive comprises an effective amount of Carboxy Methyl Cellulose in the form of about 5 pounds of CMC 7MT per ton of dry fiber weight. CMC 7MT is supplied by Hercules Corp. The wettability agent comprises an effective amount of Dodecylphenoxy poly(ethylenoxy) ethanol in the form of about 2 pounds of IGEPAL per ton of dry fiber weight. IGEPAL is supplied by Rhone Poulence of Cranbury, N.J. The Softness additive comprises an effective amount of Quaternary ammonium compound in the form of about 2 pounds of DTDMAMS per ton of dry fiber weight. DTDMAMS (Dihydrogenated Tallow Dimethyl Ammonium Methyl Sulfate) is supplied by Sherex of Dublin, Ohio.

Figure 9:
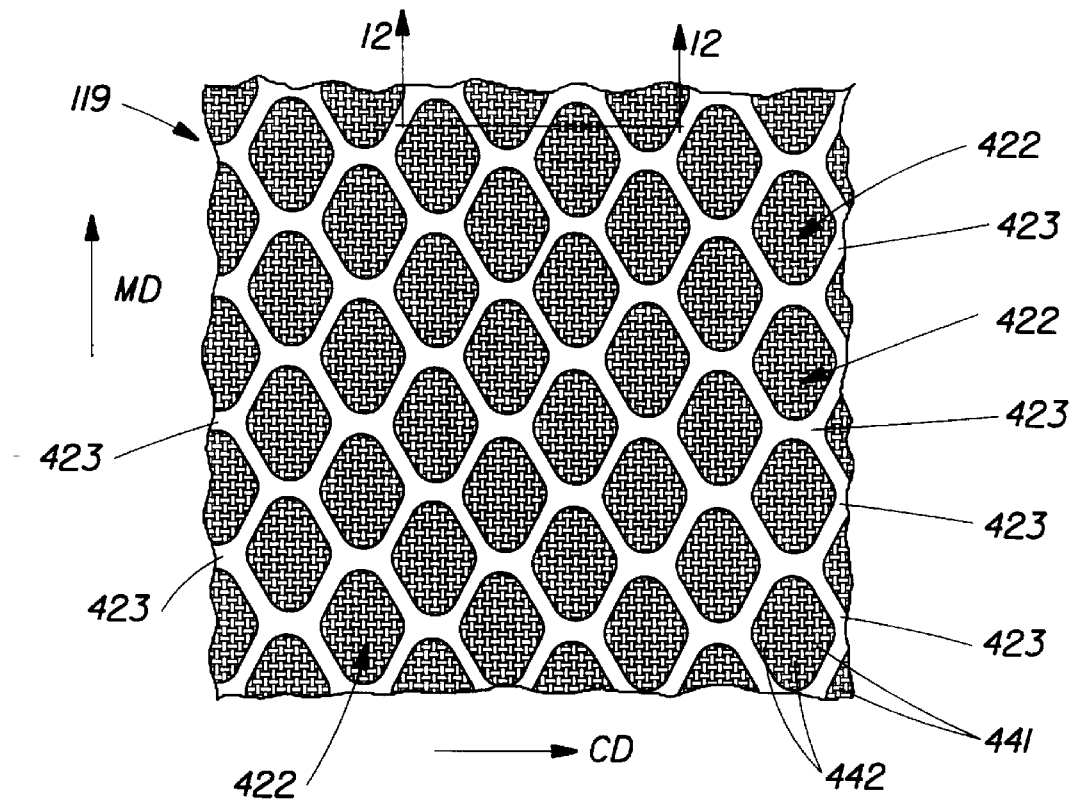
FIG. 9 is a schematic illustration of a drying member in the form of a through-air drying fabric having a macroscopically monoplanar, patterned, continuous network surface defining a plurality of discrete, isolated deflection conduits, each conduit having a machine direction length greater than the associated conduit cross machine direction width.
Figure 12:
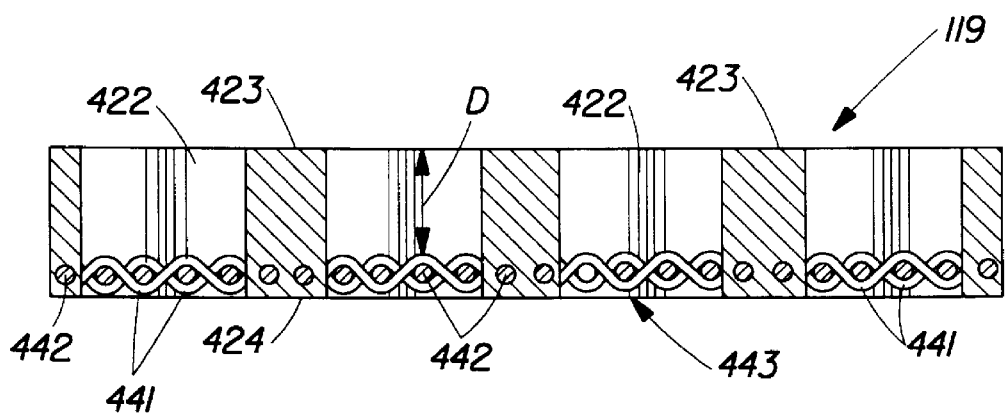
FIG. 12 is a schematic illustration of a cross-section of a drying fabric taken along lines 12—12 in FIG. 9.

When forming the web from which ply 31 is made, the slurry is deposited onto foraminous member 111 (a Fourdrinier wire of a 5 shed, satin weave configuration having 87 machine direction and 76 cross-machine direction filaments per inch), and dewatered to a consistency of about 17 percent just prior to transfer to drying member 119. The resulting embryonic web is then transferred to the drying member 119 to provide wet foreshortening of about 3 percent. The drying member 119 is in the form of a through air drying fabric as shown in FIGS. 9 and 12, such as is generally described in above referenced U.S. Pat. No. 4,529,480. The through air drying fabric has a continuous network surface 423 which defines openings of deflection conduits 422. As shown in FIG. 12, the continuous network surface 423 extends a distance D above a woven reinforcing element 443 having woven reinforcing strands 441 and 442.

The drying fabric 119 for forming the ply 31 has about 562 deflection conduits 422 per square inch as viewed in FIG. 9 (562 cells per square inch). The deflection conduits 422 have an elongated shape with a machine direction length which is about 48 mils (0.048 inch) and a cross-machine direction width of about 35 mils. The knuckle area (area of the continuous network 423) is about 36.6 percent of the surface area of the drying fabric 119 as viewed in FIG. 9. The distance D is about 22 mils.

The web is partially dried by dewatering and by predrying with through air drying apparatus 125 to a consistency of about 57 percent. The web is then adhered to the surface of yankee dryer 116, and removed from the surface of the dryer 116 by the doctor blade 117 at a consistency of about 97 percent. The yankee dryer is operated at a surface speed of about 800 feet per minute. The dry web 124 is wound onto a roll at a speed of 716 feet per minute to provide the web 131, to provide dry foreshortening of about 10 percent. The resulting web has between about 562 and about 620 relatively low density domes 184 per square inch (the number of domes 184 in the web is between zero percent to about 10 percent greater than the number of cells in the drying member 119, due to dry foreshortening of the web).

Figure 10:
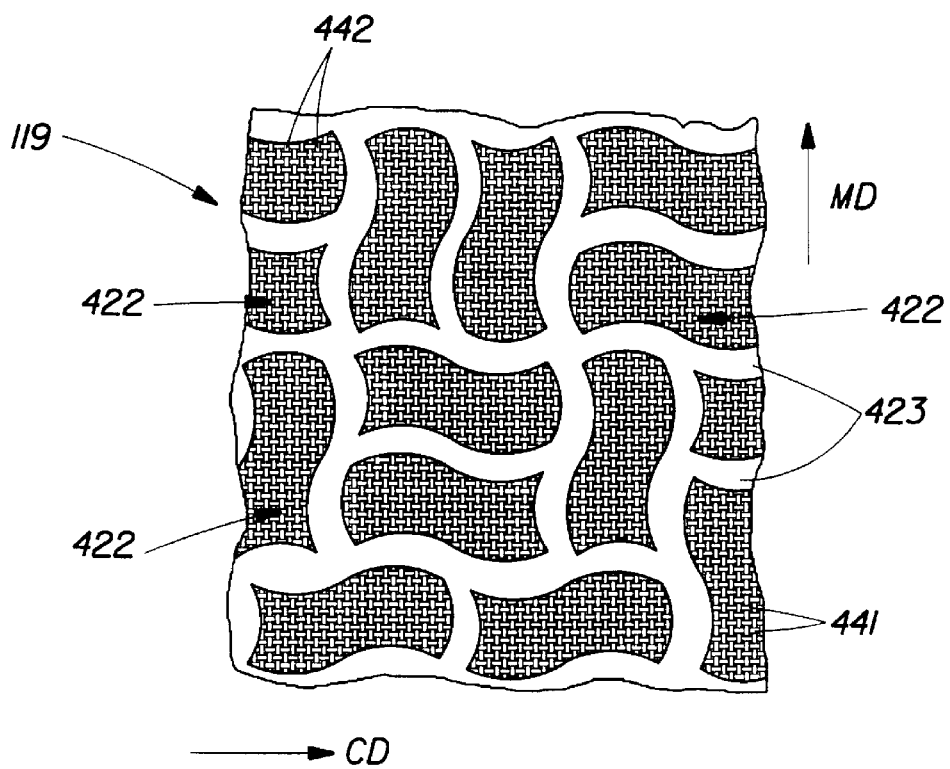
FIG. 10 is a schematic illustration of another drying member in the form of a through-air drying fabric having a continuous network surface and a plurality of discrete, isolated deflection conduits.

The ply 32 is formed from a web 132 which is made using a paper machine such as that shown in FIG. 3. The same furnish and procedure as described above with respect to ply 31 are used to form web 132, except that the drying member 119 is of the form shown in FIG. 10. Referring to FIG. 10, the drying member 119 has about 45 deflection conduits 422 per square inch, a knuckle area of about 30 percent, and a dimension D of about 30 mils. The deflection conduits 422 have a quasi-quadrilateral shape having curved sides. The deflection conduits have a length of about 191 mils and a width of about 94 mils. The web 132 has between about 45 and about 50 domes 184 per square inch. The resulting webs 131 and 132, when combined as shown in FIG. 6 to provide a 2 ply structure 20, have the following characteristics:

| Ply 31: | | Homogenous 2 ply (31-31) | |
|---|---|---|---|
| Caliper: | 12.0 | Caliper | 24.7 |
| Basis Weight: | 13.6 | Absorb. Capacity | 19.6 |
| Macro-Density: | 1.13 | Wicking Capacity: | 13.8 |
| Texture Value | 5.5 | Absorbent Rate: | 0.35 |
| Ply 32: | | Homogenous 2 ply (32-32) | |
| Caliper: | 35.0 | Caliper | 42.8 |
| Basis Weight: | 13.6 | Absorb. Capacity | 32.8 |
| Macro-Density: | 0.39 | Wicking Capacity: | 27.0 |
| Texture Value: | 24.0 | Absorbent Rate | 0.68 |
| | | Heterogenous 2 Ply 31-32: | |
| | | Caliper: | 34.6 |
| | | Absorb. Capacity | 28.1 |
| | | Wicking Capacity | 23.2 |
| | | Absorbent Rate: | 0.59 |

Units: Unless otherwise specified, caliper is reported in mils, basis weight in lbs/3000 square feet; macro-density in lb/3000 square feet-mil, Texture Value in mils, Absorbent Capacity in grams per gram, Wicking Capacity in grams per gram, and Absorbent Rate in grams per second.

Example 2

2 ply

The purpose of this example is to illustrate another method that can be used to form a two ply embodiment of the present invention.

Ply 31 is formed as follows: a 0.1 percent consistency aqueous slurry of papermaking fibers, water, and additives is formed for deposition on the foraminous member 111. The aqeuous slurry comprises a mixture of 63:20:17 by weight NSK, CTMP, and broke. The additives include a wet strength additive, a dry strength additive, a wettability agent, and a softness additive. The wet strength additive comprises an effective amount of epichlorohydrin adduct in the form of about 24 pounds KYMENE 557H per ton of dry fiber weight. The dry strength additive comprises an effective amount of Carboxy Methyl Cellulose in the form of about 5 pounds of CMC 7MT per ton of dry fiber weight. The wettability agent comprises an effective amount of Dodecylphenoxy poly(ethylenoxy) ethanol in the form of about 1.5 pounds of IGEPAL per ton of dry fiber weight. The Softness additive comprises an effective amount of Quaternary ammonium compound in the form of about 1.3 pounds of DTDMAMS per ton of dry fiber weight.

When forming the web from which ply 31 is made, the slurry is deposited onto foraminous member 111 (a Fourdrinier wire of a 5 shed, satin weave configuration having 87 machine direction and 76 cross-machine direction filaments per inch), and dewatered to a consistency of about 17 percent just prior to transfer to drying member 119. The resulting embryonic web is then transferred to the drying member 119 to provide wet foreshortening of about 3 percent. The drying member 119 is in the form of a through air drying fabric as shown in FIGS. 9 and 12, and such as is generally described in above referenced U.S. Pat. No. 4,529,480.

The drying fabric 119 for forming the ply 31 has about 240 deflection conduits 422 per square inch as viewed in FIG. 9 (240 cells per square inch). The knuckle area (area of the continuous network 423) is about 25 percent of the surface area of the drying fabric 119 as viewed in FIG. 9. The distance D is about 22 mils.

The web is partially dried by dewatering and by predrying with through air drying apparatus 125 to a consistency of about 63 percent. The web is then adhered to the surface of yankee dryer 116, and removed from the surface of the dryer 116 by the doctor blade 117 at a consistency of about 97 percent, and to provide a dry foreshortening of about 10 percent. The resulting web has a basis weight of about 13.1 pound/3000 square feet. The resulting web has between about 240 and about 262 relatively low density domes 184 per square inch (the number of domes 184 in the web is between zero percent to about 10 percent greater than the number of cells in the drying member 119, due to dry foreshortening of the web).

Ply 32 is formed as follows: a 0.1 percent consistency aqueous slurry of papermaking fibers, water, and additives is formed for deposition on the foraminous member 111. The aqeuous slurry comprises a mixture of 65.6:23.1:11.3 by weight NSK, CTMP, and broke. The additives include a wet strength additive, a dry strength additive, a wettability agent, and a softness additive. The wet strength additive comprises an effective amount of epichlorohydrin adduct in the form of about 19.5 pounds KYMENE 557H per ton of dry fiber weight. The dry strength additive comprises an effective amount of Carboxy Methyl Cellulose in the form of about 3.8 pounds of CMC 7MT per ton of dry fiber weight. The wettability agent comprises an effective amount of Dodecylphenoxy poly(ethylenoxy) ethanol in the form of about 1.4 pounds of IGEPAL per ton of dry fiber weight. The Softness additive comprises an effective amount of Quaternary ammonium compound in the form of about 1.08 pounds of DTDMAMS per ton of dry fiber weight.

Figure 11:
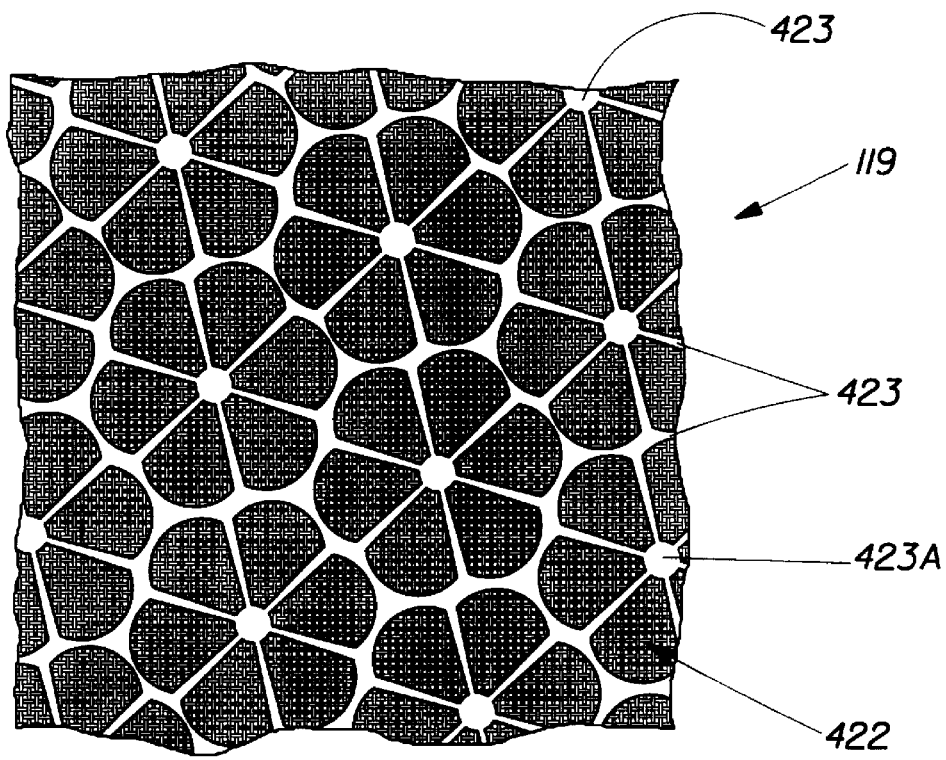
FIG. 11 is a schematic illustration of another drying member in the form of a through air drying fabric having a continuous network surface and a plurality of discrete, isolated deflection conduits.

When forming the web from which ply 32 is made, the slurry is deposited onto foraminous member 111 (a Fourdrinier wire of a 5 shed, satin weave configuration having 87 machine direction and 76 cross-machine direction filaments per inch), and dewatered to a consistency of about 17 percent just prior to transfer to drying member 119. The resulting embryonic web is then transferred to the drying member 119 to provide wet foreshortening of about 2.5 percent. The drying member 119 is in the form of a through air drying fabric as shown in FIGS. 11 and 12, and such as is generally described in above referenced U.S. Pat. No. 4,529,480.

The drying fabric 119 for forming the ply 32 has about 97 deflection conduits 422 per square inch as viewed in FIG. 11 (97 cells per square inch). The knuckle area (area of the continuous network 423) is about 20 percent of the surface area of the drying fabric 119 as viewed in FIG. 11. The distance D is about 15.9 mils.

The web is partially dried by dewatering and by predrying with through air drying apparatus 125 to a consistency of about 63 percent. The web is then adhered to the surface of yankee dryer 116, and removed from the surface of the dryer 116 by the doctor blade 117 at a consistency of about 97 percent, and to provide a dry foreshortening of about 4.5 percent. The resulting web has a basis weight of about 16.1 pound/3000 square feet. The resulting web has between about 97 and about 102 relatively low density domes 184 per square inch.

The resulting webs 131 and 132, when combined as shown in FIG. 6 to provide a 2 ply structure 20, have the following characteristics:

| Ply 31: | | Homogenous 2 ply (31-31) | |
|---|---|---|---|
| Caliper: | 16.0 | Caliper | 27.0 |
| Basis Weight: | 13.1 | Absorb. Capacity | 25.9 |
| Macro-Density: | 0.82 | Wicking Capacity: | 17.2 |
| Texture Value | 15.3 | Absorbent Rate: | 0.48 |
| Ply 32: | | Homogenous 2 ply (32-32) | |
| Caliper: | 22.0 | Caliper | 30.0 |
| Basis Weight: | 16.1 | Absorb. Capacity | 24.7 |
| Macro-Density: | 0.73 | Wicking Capacity: | 14.5 |
| Texture Value: | 26.8 | Absorbent Rate | 0.64 |
| | | Heterogenous 2 Ply 31-32: | |
| | | Caliper: | 27.9 |
| | | Absorb. Capacity | 26.7 |
| | | Wicking Capacity | 22.0 |
| | | Absorbent Rate: | 0.65 |

Example 3

3 ply

The purpose of this example is to illustrate one method that can be used to form a three ply embodiment of the present invention. Referring to FIG. 2A, the plies 41A and 41B are formed from webs made on a paper machine, such as that shown in FIG. 3, having a drying member 119 in the form of a through air drying fabric. The ply 42 is formed from a web made on a paper machine, such as that shown in FIG. 3, having a drying member 119 in the form of a conventional papermakers dewatering felt.

The following procedure is used to make the webs from which plies 41A and 41B are formed. A 0.1 percent aqueous slurry of papermaking fibers, water, and additives is formed for deposition on the foraminous member 111. The aqeuous slurry comprises a mixture of 75:25 by weight NSK (northern softwook Kraft) and SSK (southern softwood kraft) paper fibers. The additives include a wet strength additive and a dry strength additive. The wet strength additive comprises an effective amount of epichlorohydrin adduct in the form of about 22 pounds KYMENE 557H per ton of dry fiber weight. The dry strength additive comprises an effective amount of Carboxy Methyl Cellulose in the form of about 5 pounds of CMC 7MT per ton of dry fiber weight.

The slurry is deposited onto foraminous member 111 (a Fourdrinier wire of a 5 shed, satin weave configuration having 87 machine direction and 76 cross-machine direction filaments per inch), and dewatered to a consistency of about 17 percent. The resulting embryonic web is then transferred to the drying member 119, which is in the form of a through air drying fabric as shown in FIG. 11. The drying fabric 119 for forming the plies 141A and 141B has about 75 deflection conduits 422 per square inch as viewed in FIG. 11. The knuckle area (area of the continuous network 423) is about 39 percent of the surface area of the drying fabric 119 as viewed in FIG. 11. The distance D is about 16 mils.

The web is partially dried by dewatering and by predrying with through air drying apparatus 125 to a consistency of about 57 percent. The web is then adhered to the surface of yankee dryer 116, and removed from the surface of the dryer 116 by the doctor blade 117 at a consistency of about 97 percent. The yankee dryer is operated at a speed of about 800 feet per minute. The dry web 124 is wound onto a roll at a speed of 716 feet per minute to provide the web 141A (or 141B), with dry foreshortening being about 10 percent. The web 141A (or 141B) has between about 75 and about 85 domes 184 per square inch.

The following procedure is used to make the web from which ply 42 is formed. A 0.1 percent aqueous slurry of papermaking fibers, water, and additives is formed for deposition on the foraminous member 111. The aqeuous slurry comprises a mixture of 60:40 by weight NSK and CTMP. The additives include a wet strength additive, a dry strength additive, a wettability agent, and a softness additive. The wet strength additive comprises an effective amount of epichlorohydrin adduct in the form of about 22 pounds KYMENE 557H per ton of dry fiber weight. The dry strength additive comprises an effective amount of Carboxy Methyl Cellulose in the form of about 3.7 pounds of CMC 7MT per ton of dry fiber weight. The wettability agent comprises an effective amount of Dodecylphenoxy poly (ethylenoxy) ethanol in the form of about 2 pounds of IGEPAL per ton of dry fiber weight. The Softness additive comprises an effective amount of Quaternary ammonium compound in the form of about 5 pounds of DTDMAMS per ton of dry fiber weight.

The slurry is deposited onto foraminous member 111 (a Fourdrinier wire of a 5 shed, satin weave configuration having 87 machine direction and 76 cross-machine direction filaments per inch), and dewatered to a consistency of about 14 percent. The resulting embryonic web is then transferred to the drying member 119, which is in the form of a conventional papermakers dewatering felt having a relatively smooth web support surface. The felt is an Albany XYJ 1605-7 felt (precompressed) supplied by Albany International Corporation.

The web is partially dried by dewatering and pressing the web and felt to provide an intermediate web having a consistency of about 39 percent. The web is then adhered to the surface of yankee dryer 116, and removed from the surface of the dryer 116 by the doctor blade 117 at a consistency of about 96 percent. The yankee dryer is operated at a speed of about 3200 feet per minute. The dry web 124 is wound onto a roll at a speed of 2712 feet per minute to provide the web 142. The web 142 is dry foreshortened about 15 percent.

The resulting webs 141A, 142, and 141B, when combined as shown in FIGS. 7 and 8 to provide a 3 ply structure 20, have the following characteristics:

| Ply 41A (or 41B): | | Homog. 3 ply (41A-41A-41A) | |
|---|---|---|---|
| Caliper: | 25.4 | Caliper | 38.3 |
| Basis Weight: | 13.6 | Absorb. Capacity | 23.5 |
| Macro-Density: | 0.535 | Wicking Capacity: | 16.8 |
| Texture Value | 17.7 | Absorbent Rate | 0.96 |
| Ply 42: | | Homog. 3 ply (42-42-42) | |
| Caliper: | 6.0 | Caliper | 26.6 |
| Basis Weight: | 12.5 | Absorb. Capacity | 15.4 |
| Macro-Density: | 2.08 | Wicking Capacity: | 8.27 |
| Texture Value: | <1.0 | Absorbent Rate | 0.24 |
| | | Heterogenous 3 Ply 41A-42-41B: | |
| | | Caliper: | 40.8 |
| | | Absorb. Capacity | 26.5 |
| | | Wicking Capacity: | 17.7 |
| | | Absorbent Rate: | 0.86 |

Example 4

3 ply

The purpose of this example is to illustrate an alternative three ply embodiment such as that shown in FIG. 2B. The three ply embodiment of this example includes a patterned, relatively textured ply 41 disposed between two substantially unpatterned, relatively untextured plies 42A and 42B. Ply 41 is formed from the same type web from which plies 41A and 41B are formed in Example 3. Plies 42A and 42B are formed from the same type web from which ply 42 is formed in Example 3. The resulting heterogenous 3 ply paper product has the following properties:

| Heterogenous 3 Ply 42A-41-42B: | |
|---|---|
| Caliper: | 27.8 |
| Absorb. Capacity | 22.6 |
| Wicking Capacity: | 13.4 |
| Absorbent Rate: | 0.6 |

In alternative embodiments of Examples 3 and 4, the ply 42 in Example 3, and the plies 42A and 42B in Example 4 can be made from webs having multiple basis weight regions with a high basis weight region comprising an essentially continuous network, as described in U.S. Pat. No. 5,503,715 to Trokhan. The webs from which the plies 42, 42A and 42B are obtained can be formed by depositing an aqueous slurry onto a foraminous member 111 which comprises a plurality of discrete protuberances joined to a reinforcing structure, each protuberance having an orifice (as is described generally in U.S. Pat. No. 5,503,715). One suitable forming member 111 includes about 200 protuberances per square inch, each protuberance extending a distance D of about 5.5 mils above the reinforcing structure. The top surface areas of the protuberances comprise about 28 percent of the surface area of the drying member (knuckle area of the protuberances is about 28 percent). The reinforcing structure can be a 90×72 triple layer construction woven wire, available from the Appleton Wire Company.

TEST PROCEDURES

Samples are placed in a temperature (73±2 Fahrenheit) and relative humidity (50±2 percent) controlled location for at least 2 hours prior to testing. Testing is conducted under these conditions.

Absorbent Capacity

The absorbent capacity is a measure of the ability of a paper structure, while supported horizontally, to hold liquid. The absorbent capacity is measured using the following procedure: A full size (11 inch×11 inch) sheet is supported horizontally in a tared filament lined basket and weighed to provide the weight of the dry sheet. The filament lined basket has crossed filaments which serve to support the sheet horizontally. The crossed filaments permit unrestricted movement of water into and out of the paper sheet. The sheet supported in the basket is lowered into a distilled water bath having a temperature of 73±2 degrees F for one minute. The basket is then raised from the bath, so that the sheet is allowed to drain for 1 minute. The basket and sheet are then re-weighed to obtain the weight of the water absorbed by the sheet. The absorbent capacity, in grams/gram, is calculated by dividing the weight of the water absorbed by the sheet by the weight of the dry sheet. The absorbent capacity is reported as an average of at least 8 measurements.

Absorbent Rate and Wicking Capacity

The absorbent rate is a measure of the rate at which a paper structure acquires liquid by wicking. The wicking capacity is a measure of the weight of water wicked into a sample per gram of sample dry weight. The absorbent rate and wicking capacity are measured using the following procedure. The sample sheet, which is cut into a circular shape having a 3 inch diameter, is supported horizontally on a tared filament tray. The weight of the dry sample is determined.

A vertical tube having a diameter of 0.312 inches and holding a column of distilled water is provided. The tube is supplied with water from a reservoir to provide a convex meniscus adjacent the lip of the tube. The water level in the tube is adjustable, such as by a pump, so that the meniscus can be raised to contact a sample sheet positioned above the lip of the tube.

The sample sheet supported in the filament tray is positioned above the vertical tube, such the the filament tray is about ⅛ inch above the lip of the tube. The water level in the tube is then varied so that the meniscus contacts the sample, after which the pressure used to raise the meniscus (about 2 psi) is reduced to zero. The weight of the sample sheet is monitored as water is taken up by the sample. Time zero is set at the instant when the sample first takes up water (first change in balance reading from dry weight). At time equals two seconds (two seconds after time zero), the contact between the meniscus and the sample sheet is broken by suction (about 2 psi) applied to the water in the tube, and the wetted sample weight is recorded. The wetted sample is weighed after breaking contact between the meniscus and the sample so as not to include surface tension in the weight measurement.

The absorbent rate is the weight of the wetted sample minus the sample dry weight, divided by 2 seconds. A small positive pressure (about 2 psi) is applied to the water in the tube to cause the meniscus to recontact the sample. The weight of the sample is again monitored until time equals 180 seconds. At time equals 180 seconds, the contact between the meniscus and the sample sheet is broken by suction (about 2 psi) applied to the water in the tube, and the wetted sample weight is again recorded. The wetted sample is weighed after breaking contact between the meniscus and the sample so as not to include surface tension in the weight measurement. The wicking capacity is calculated as the wetted sample weight at 180 seconds minus the dry weight, divided by the dry weight. The absorbent capacity and wicking capacity are each reported as an average of at least 4 measurements.

Texture Value

The texture value is a measurement of the non-embossed, wet formed texture of a surface of a tissue paper web. Each surface of a ply can be measured and assigned a texture value. Generally, if only one texture value is provided, it is the higher texture value for the two surfaces of a ply. Mechanically embossed texture, such as that imparted to the plies when the plies are combined, is not measured The texture value of a surface is determined by scanning a surface of a ply with a transmitted light microscope, and determining the elevation difference between a local high point (peak) and an adjacent local low point (valley) in a particular field of view. The texture value of the surface of a ply is preferably measured prior to combining a ply with other plies to form a multiple ply product. However, the texture value can also be obtained from a sample cut from a multiple ply sample, provided that any texture features created by combining the plies (e.g. embossing) are not included in the measurement.

The elevation difference is determined by varying the focus of the microscope, and recording the difference in focus positions between the peaks and adjacent valleys in the field of view. The measurements are made on a sample measuring about 2 inches by 1.5 inches. The difference between 15 adjacent peaks and valleys are measured and averaged to provide the texture value for the surface. A 10× eyepiece and a 10× objective (numerical aperture=0.30) is used for samples having more than about 150 peaks per square inch, and a 10× eyepiece and 5× objective (numerical aperture=0.15) is used for samples having less than about 150 peaks per square inch. A suitable microscope which has an readout indicating the difference in elevation between two focus settings is a Zeis Axioplan Transmitted Light Microscope with a Microcode II Accessory. The Microcode accessory records the range of focus settings in millimeters, which can then be converted to mils.

For instance, where the sample includes the wet formed domes 184 and network 183, the microscope focus would be varied to bring into focus the top of a dome 184. The microscope focus would then be varied to bring into focus the surface of an adjacent portion of the network 183. The difference in elevation for the dome and adjacent network would be recorded. This process would be repeated to provide 15 dome/network elevation differences. The 15 elevation differences are then averaged to provide the texture value of the surface. The difference in elevation between a dome and adjacent network surface is represented as E in FIG. 5.

Caliper

The caliper of a single or multiple ply sample is a measurement of thickness under a prescribed loading. The caliper of a ply is measured using the following procedure: A dial indicator is used to measure the thickness of the sample under a compressive loading of 95 grams per square inch provided by a foot having a 2 inch diameter. The caliper is reported as the average of at least 8 such measurements.

Basis Weight

The basis weight is a measure of the weight per unit area of a sample. The basis weight of a sample is measured using the following procedure. A total of eight plies of 4 inch by 4 inch squares of the sample are weighed, to provide a weight per 128 square inches of the substrate (4×4×8). This weight per 128 square inches is then converted to units of pounds per 3000 square feet. The basis weight is reported as an average of 4 such measurements.

Macro-Density

The macro-density is the basis weight of a sample divided by its caliper.

What is claimed:

1. A multiple ply tissue product comprising:
   a first ply comprising a paper web having a patterned, continuous network region having a relatively high density and discrete regions dispersed throughout and isolated one from another by the continuous network region, the discrete regions having relatively low densities; and
   a second ply, wherein the second ply does not include a patterned, continuous network region having a relatively high density and discrete regions dispersed throughout and isolated one from another by the continuous network region.

2. The multiple ply tissue paper product of claim 1 wherein the first ply has a caliper which is at least 1.25 times the caliper of the second ply.

3. The multiple ply tissue paper product of claim 2 wherein the caliper of the first ply is at least 1.5 times the caliper of the second ply.

4. The multiple ply tissue paper product of claim 3 wherein the caliper of the first ply is least 2.0 times the caliper of the second ply.

5. The multiple ply tissue paper product of claim 1 wherein second ply has a macro-density which is at least 1.5 times the macro-density of the first ply.

6. The multiple ply tissue paper product of claim 5 wherein the second ply has a macro-density of at least 2.5 times the macro-density of the first ply.

7. A multiple ply tissue product comprising:
   a first ply comprising a paper web having a patterned, continuous network region having a relatively high density; and X discrete relatively low density regions dispersed throughout and isolated one from another by the continuous network region, the value of X being between 10 and 600; and
   a second ply, wherein the second ply does not include a continuous network region having a relatively high density and discrete regions dispersed throughout and isolated one from another by the continuous network region.

8. The tissue product of claim 7 wherein the value of X is less than 200.

9. A multiple ply tissue product comprising:
   a first ply;
   a second ply; and
   a third ply disposed intermediate the first and second plies;
   wherein each of the first and second plies comprises a paper web having a patterned, continuous network region having a relatively high density and discrete regions dispersed throughout and isolated one from another by the continuous network region, the discrete regions having relatively low densities; and
   wherein the third ply does not include a patterned, continuous network region having a relatively high density and discrete regions dispersed throughout and isolated one from another by the continuous network region.

10. A multiple ply tissue product comprising:
    a first ply;
    a second ply; and
    a third ply disposed intermediate the first and second plies;
    wherein the third ply comprises a paper web having a patterned, continuous network region having a relatively high density and discrete regions dispersed throughout and isolated one from another by the continuous network region, the discrete regions having relatively low densities; and
    wherein neither of the first and second plies comprises a continuous network region having a relatively high density and discrete regions dispersed throughout and isolated one from another by the continuous network region.

* * * * *

UNITED STATES PATENT AND TRADEMARK OFFICE
CERTIFICATE OF CORRECTION

PATENT NO. : 5,830,558
DATED : November 3, 1998
INVENTOR(S) : Steven Lee Barnholtz It is certified that error appears in the above-identified patent and that said Letters Patent is hereby corrected as shown below:

Column 2, line 14, delete "multiply" and insert therefor -- multi-ply --.

Column 16, line 38, delete "73±2" and insert therefor -- 73 +/- 2 --.

Column 16, line 39, delete "50±2" and insert therefor -- 50 +/- 2 --.

Column 16, line 53, delete "73±2" and insert therefor -- 73 +/- 2 --.

Signed and Sealed this

Eleventh Day of May, 1999

Attest:

Q. TODD DICKINSON

*Attesting Officer*   *Acting Commissioner of Patents and Trademarks*